(12) United States Patent
Sanchez et al.

(10) Patent No.: US 9,920,077 B2
(45) Date of Patent: Mar. 20, 2018

(54) AMINE SUBSTITUTED TRISILYLAMINE AND TRIDISILYLAMINE COMPOUNDS AND SYNTHESIS METHODS THEREOF

(71) Applicants: Antonio Sanchez, Branchburg, NJ (US); Jean-Marc Girard, Paris (FR)

(72) Inventors: Antonio Sanchez, Jersey City, NJ (US); Jean-Marc Girard, Versailles (FR); Gennadiy Itov, Branchburg, NJ (US); Manish Khandelwal, Branchburg, NJ (US); Matthew Damien Stephens, Branchburg, NJ (US); Peng Zhang, Branchburg, NJ (US)

(73) Assignee: L'Air Liquide, SociétéAnonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/025,198

(22) PCT Filed: Sep. 19, 2014

(86) PCT No.: PCT/US2014/056618
§ 371 (c)(1),
(2) Date: Mar. 25, 2016

(87) PCT Pub. No.: WO2015/047914
PCT Pub. Date: Apr. 2, 2015

(65) Prior Publication Data
US 2016/0237099 A1 Aug. 18, 2016

Related U.S. Application Data

(60) Provisional application No. 61/883,452, filed on Sep. 27, 2013.

(51) Int. Cl.
C07F 5/06 (2006.01)
C07F 7/02 (2006.01)
C07F 7/10 (2006.01)
H01L 21/02 (2006.01)

(52) U.S. Cl.
CPC .............. *C07F 7/025* (2013.01); *C07F 7/10* (2013.01); *H01L 21/02617* (2013.01)

(58) Field of Classification Search
CPC ..... C07F 7/07; C07F 7/10; C09K 3/00; B01D 15/08; G01N 33/00
USPC ............... 510/175, 499; 423/210, 228, 246; 585/860; 556/175, 499
See application file for complete search history.

(56) References Cited

U.S. PATENT DOCUMENTS

| 4,675,424 A | 6/1987 | King, III et al. |
| 5,413,813 A | 5/1995 | Cruse et al. |
| 5,874,368 A | 2/1999 | Laxman et al. |
| 7,638,645 B2 | 12/2009 | Gordon et al. |
| 7,838,329 B2 | 11/2010 | Hunks et al. |
| 8,357,430 B2 | 1/2013 | Dussarrat et al. |
| 2005/0070717 A1 | 3/2005 | Wasserscheid et al. |
| 2005/0181633 A1 | 8/2005 | Hochberg et al. |
| 2006/0222583 A1 | 10/2006 | Hazeltine |
| 2007/0010072 A1* | 1/2007 | Bailey .................. C23C 16/308 438/478 |
| 2008/0045723 A1 | 2/2008 | Cassol et al. |
| 2008/0241575 A1 | 10/2008 | Lavoie et al. |
| 2009/0075490 A1 | 3/2009 | Dussarrat et al. |
| 2009/0137100 A1 | 5/2009 | Xiao et al. |
| 2009/0256127 A1 | 10/2009 | Feist et al. |
| 2009/0291872 A1* | 11/2009 | Bara .................. B01D 19/0005 510/175 |
| 2009/0291874 A1 | 11/2009 | Bara et al. |
| 2009/0299084 A1 | 12/2009 | Okubo et al. |
| 2010/0221428 A1 | 9/2010 | Dussarrat et al. |
| 2011/0129616 A1 | 6/2011 | Ingle et al. |
| 2012/0017934 A1 | 1/2012 | Kumon et al. |
| 2012/0058282 A1 | 3/2012 | Hong et al. |
| 2012/0213940 A1 | 8/2012 | Mallick |
| 2012/0220139 A1 | 8/2012 | Lee et al. |
| 2013/0089487 A1 | 4/2013 | Ritter, III |
| 2013/0143018 A1 | 6/2013 | Tan et al. |
| 2013/0189854 A1 | 7/2013 | Hausmann et al. |
| 2013/0224097 A1 | 8/2013 | Miller |
| 2013/0323435 A1 | 12/2013 | Xiao et al. |
| 2014/0051264 A1 | 2/2014 | Mallick et al. |
| 2014/0193953 A1 | 7/2014 | Lavoie |

FOREIGN PATENT DOCUMENTS

| DE | 1 158 972 | 12/1964 |
| EP | 2 000 561 | 12/2008 |

(Continued)

OTHER PUBLICATIONS

International Search Report and Written Opinion for corresponding PCT/US2014/056618, dated Dec. 12, 2014.
Cradock, S. et al., "Reactions of tin(IV) chloride with silyl compounds. I. Reactions with inorganic silyl compounds," Journal of the Chemical Society Dalton Transactions, Jan. 1975, 1624-1628.
Andreev, A.A. et al., "Direct electrophilic silylation of terminal alkynes," Organic Letters 2004, vol. 6, No. 3, 421-424 and SI1-SI5.
Felch, S.B. et al., "Plasma doping for the fabrication of ultra-shallow junctions," Surface and Coatings Technology 156 (2002) 229-236.

(Continued)

*Primary Examiner* — Sudhakar Katakam
*Assistant Examiner* — Kofi Adzamli
(74) *Attorney, Agent, or Firm* — Patricia E. McQueeney (57) ABSTRACT

Halogen free amine substituted trisilylamine and tridisilylamine compounds and a method of their preparation via de-hydrogenative coupling between the corresponding unsubstituted trisilylamines and amines catalyzed by transition metal catalysts is described. This new approach is based on the catalytic dehydrocoupling of a Si—H and a N—H moiety to form an Si—N containing compound and hydrogen gas. The process can be catalyzed by transition metal heterogenous catalysts such as Ru(0) on carbon, Pd(0) on MgO) as well as transition metal organometallic complexes that act as homogeneous catalysts. The —Si—N containing products are halide free. Such compounds can be useful for the deposition of thin films by chemical vapor deposition or atomic layer deposition of Si containing films.

7 Claims, 2 Drawing Sheets

(56) References Cited

FOREIGN PATENT DOCUMENTS

| KR | 10 2012 0024473 | 3/2012 |
|---|---|---|
| KR | 10 2012 0099270 | 9/2012 |
| KR | 10 2013 0135793 | 12/2013 |
| KR | 10 2014 0057908 | 5/2014 |
| WO | WO 2006 136584 | 12/2006 |
| WO | WO 2007 008705 | 1/2007 |
| WO | WO 2009 087609 | 7/2009 |
| WO | WO 2011 056519 | 5/2011 |
| WO | WO 2015 190749 | 12/2015 |

OTHER PUBLICATIONS

Godleski, S.A., et al., "MNDO study of phosphine- and amine-substituted silicenium ions", Tetrahedron Letter (1982) 23(43) 4453-3356.

Ishii, K. et al., "Growth of polycrystalline hexagonal-close-packed Co films on glass substrates from low kinetic energy vapor," Journal of Vacuum Science & Technology A 16 (1998) 759-762.

Lee, J. et al., "A hydrogen gas sensor employing vertically aligned $TiO_2$ nanotube arrays," Sensors and Actuators B 160 (2011) 1494-1498.

Scantlin, W.M., et al., "The borane-catalyzed condensation of trisilazane and N-methyldisilazane", Inorganic Chemistry (1972) 11(12) 3028-2084.

Scantlin, W.M., et al., "Pentaborane(9)-catalyzed condensation of silylamines", Journal of the Chemical Society D: Chemical Communications (1971) (20) 1246.

Schmidbauer, H. et al., "Difference in reactivity of 1,4-disilabutane and $n$-tetrasilane towards secondary amines," Z. Naturforsch. 45b 1990 1679-1863.

Sommer, L.H. et al, "Stereochemistry of asymmetric silicon. XVI. Transition metal catalyzed substitute reactions of optically active organosilicon hydrides," Journal of the American Chemical Society 91:25 Dec. 3, 1969 7061-7067.

Toh, C.K. et al., "Ruthenium carbonyl-catalysed Si—heteratom X coupling (X= S, 0, N)," Journal of Organometallic Chemistry 717 (2012) 9-13.

International Search Report and Written Opinion for related PCT/US2016/025010, dated Jul. 15, 2016.

International Search Report and Written Opinion for related PCT/US2016/037006, dated Sep. 12, 2016.

International Search Report and Written Opinion for related PCT/US2016/037013, dated Sep. 12, 2016.

\* cited by examiner

AMINE SUBSTITUTED TRISILYLAMINE AND TRIDISILYLAMINE COMPOUNDS AND SYNTHESIS METHODS THEREOF

CROSS REFERENCE TO RELATED APPLICATIONS

This application is a 371 of International PCT Application PCT/US2014/056618, filed Sep. 19, 2014, which claims priority from U.S. Provisional Patent Application No. 61/883,452 filed on Sep. 27, 2013, the entire contents of each being incorporated herein by reference.

BACKGROUND OF THE INVENTION

Most of processes found in the literature to form silicon-heteroatom and germanium heteroatom bonds involve the reaction of a chlorosilane and a nucleophile (amine, phosphine, etc). These reactions are based on a net dehydrohalogenation thus forming one equivalent of a hydrogen halide which needs to be scavenged by a base, forming large amounts of salt which needs to be filtered out. This fact also limits the scope of the reaction to base-compatible substrates and results in products contaminated with a halogen such as chlorine and aminohalogens.

Silane compounds such as monosilane, disilane and trisilane are used in a variety of applications. In the field of semiconductors, silane compounds are frequently used as starting materials for the production by chemical vapor deposition (CVD) of silicon-based dielectric or semiconductor films of, e.g., silicon nitride, silicon oxide, or silicon oxynitride. More specifically, silane compounds can produce silicon nitride by reaction with a nitrogen-containing reaction gas such as ammonia, silicon oxide by reaction with an oxygen-containing gas such as oxygen, and silicon oxynitride by reaction with a nitrogen-containing gas and an oxygen-containing gas.

At present the standard method for producing silicon nitride films by CVD involves inducing a reaction between ammonia gas or other amine (the amino compound) and a halosilane such as chlorosilane (the silane compound); however, ammonium chloride or amine hydrochloride is produced as a by-product by this reaction. Ammonium chloride is a white solid and as such accumulates in and clogs the exhaust lines of the CVD reaction apparatus. Amine hydrochloride salts are highly undesirable contaminants in aminosilanes used for electrical applications because they can react with metals in the CVD chamber and degrade the electrical properties of the semiconductor material or lead the creation of other types of defects. More than that, these salts are known to sublimate by a dissociation-recombination process generating HCl. Hydrogen chloride is a corrosive gas that can damage any process taking place in the CVD chamber as well as the chamber itself. Reactive chlorine from these an any other sources may cause these deleterious effects.

In CVD methods, it is therefore desired to have a starting material that is halogen-free.

DETAILED DESCRIPTION OF THE INVENTION

Figure 1:
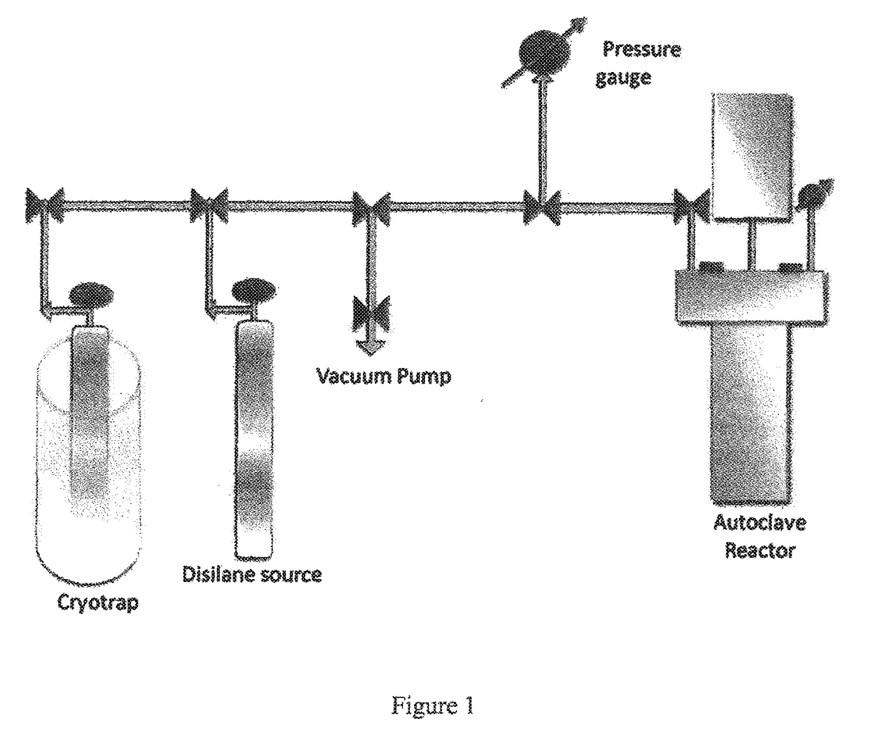
FIG. 1 is a typical reactor apparatus wherein the reaction vessel is an autoclave reactor fitted with a stirrer and connected to a manifold capable of providing vacuum and reactants.
Figure 2:
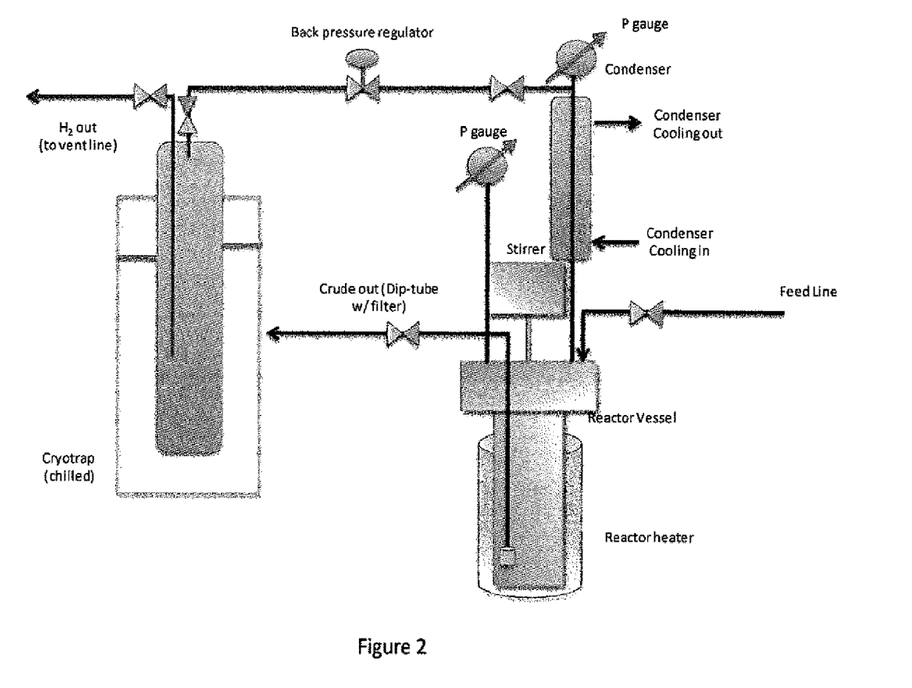
FIG. 2 is a typical reactor apparatus wherein the reactor vessel is attached to a condenser allowing for hydrogen venting and a Dip-tube with filter for removal of the product.

A method for the synthesis of compounds having silicon-nitrogen bonds without the formation of halogen salt byproducts has been developed. All of the compounds produced by method of synthesis described and claimed herein are "halogen free" as that term is defined herein. This approach is based on the catalytic dehydrocoupling of hydrogen to form gas and a nitrogen silicon bond. The process is catalyzed by transition metal catalysts. Catalysts may be heterogeneous or homogeneous. The general reaction for a secondary amine is given by equation 1. The general reaction is given in equation 1. The reaction of equation 1 is exothermic. The reaction may be carried out in a solvent or without a solvent. The reaction may be carried out in a batch or continuous flow reactor. When a batch reactor is used, the reactor may be attached to a condenser connected to a cryotrap (FIG. 2). In this assembly, the formed hydrogen can be vented as the reaction takes place. The pressure can be controlled by a back pressure regulator attached between the condenser and the cryotrap. The cryotrap can be connected to a vent line allowing sending hydrogen out of the system during and/or after the reaction. The Dip-tube with filter permits easy removal of the product from the vessel.

The term "amine" as used throughout this specification always refers to a secondary amine unless otherwise indicated.

$$(H_3Si)_3N + n HNR^1R^2 + m HNR^3R^4 + k HNR^5R^6 = (R^1R^2N)_n(R^3R^4N)_m(R^5R^6N)_k(NSi_3H_{(9-n-m-k)}) + (n+m+k+)H_2 \quad 1.$$

where n=1 to 3; m=0 to 3; k=0 to 3; $R^1$, $R^3$, and $R^5$ are independently selected from the group of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^1R^2N$, $R^3R^4N$ and $R^5R^6N$ can be cyclic secondary amines include aziridine, azetidine, piperidine, pyrrolidine, pyrrole, imidazole, pyrazole, indole or any C-substituted derivatives of the cyclic secondary amine $R^2$, $R^4$, and $R^6$ are independently selected from the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted cyclic secondary amines include aziridine, azetidine, piperidine, pyrrolidine, pyrrole, imidazole, pyrazole, indole or any C-substituted derivatives of the cyclic secondary amine.

A non-limiting list of the members of the alkyl substituent groups comprises: methyl, ethyl, propyl, iso-propyl, butyl, tert-butyl, sec-butyl, iso-butyl, pentyl, neopentyl, isopentyl, hexyl, isohexyl A non-limiting list of the members of the aryl substituent groups comprises: phenyl, tolyl, xylyl, napthyl, pyridyl.

Alkenyl is defined as any univalent aliphatic hydrocarbon radical $C_nH_{2n-1}$ (such as 2-butenyl $CH_3CH:CHCH_2-$) derived from an alkene by removal of one hydrogen atom. Where n=2 to 8.

Alkynyl is defined as any of a series of open chain hydrocarbons with a carbon-carbon triple bond and the general formula $C_nH_{2n-2}$. Where n=2 to 8.

Depending on the structure of the amine compound and structure of the Si compound and the molar ratio of Si to N a number of molecules containing Si—N bonds can be formed. These molecules containing Si—N bonds may be linear or branched. Examples linear and branched combinations and a method of synthesizing each are described.

A compound having the formula:

$(R^1R^2N)_n(R^3R^4N)_m(R^5R^6N)_k(NSi_3H_{(9-n-m-k)})$;

where n=1 to 3; m=0 to 3; k=0 to 3; $R^1$, $R^3$, and $R^5$ are independently selected from the group of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_{10}$ alkyl-substituted silyl, $R^2$, $R^4$, and $R^6$ are independently selected from the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^1R^2N$, $R^3R^4N$ and $R^5R^6N$ can be cyclic secondary amines independently selected from the group aziridine, azetidine, piperidine, pyrrolidine, pyrrole, imidazole, pyrazole, indole or any C-substituted derivatives of the cyclic secondary amine. When $R^1$, $R^3$, or $R^5$ are H, the amine is a primary amine. Polysubstitution can be avoided when $R^1$, $R^3$, or $R^5$ are H if the corresponding $R^2$, $R^4$, or $R^6$ are independently selected from the group of linear or branched $C_3$ to $C_6$ alkyl, linear or branched $C_3$ to $C_8$ alkenyl, linear or branched $C_3$ to $C_8$ alkynyl, $C_6$ to $C_{10}$ aryl, linear or branched $C_3$ to $C_6$ alkyl ether, silyl, trimethyl silyl, or linear or branched $C_3$ to $C_6$ alkyl-substituted silyl, cyclic secondary amines include aziridine, azetidine, piperidine, pyrrolidine, pyrrole, imidazole, pyrazole, indole or any C-substituted derivatives of the cyclic secondary amine.

The art has described compounds that fall within the general structure described herein. All such compounds are excluded from the compound claims of the present invention. The following compound found in W. M. Scantlin and A. D. Norman Inorganic Chemistry, Vol. 11, No. 12, 3082-3084, 1972, is excluded: $[(SiH_3)_2N]_2SiH_2$.

A method for preparing a compound having the formula:

where n=1 to 3; m=0 to 3; k=0 to 3; $R^1$, $R^3$, and $R^5$ are independently selected from the group of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^2$, $R^4$, and $R^6$ are independently selected from the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^1R^2N$, $R^3R^4N$ and $R^5R^6N$ can be cyclic secondary amines independently selected from the group aziridine, azetidine, piperidine, pyrrolidine, pyrrole, imidazole, pyrazole, indole or any C-substituted derivatives of the cyclic secondary amine. When $R^1$, $R^3$, or $R^5$ are H, the amine is a primary amine. Polysubstitution can be avoided when $R^1$, $R^3$, or $R^5$ are H if the corresponding $R^2$, $R^4$, or $R^6$ are independently selected from the group of linear or branched $C_3$ to $C_6$ alkyl, linear or branched $C_3$ to $C_8$ alkenyl, linear or branched $C_3$ to $C_8$ alkynyl, $C_6$ to $C_{10}$ aryl, linear or branched $C_3$ to $C_6$ alkyl ether, silyl, trimethyl silyl, or linear or branched $C_3$ to $C_6$ alkyl-substituted silyl, cyclic secondary amines include aziridine, azetidine, piperidine, pyrrolidine, pyrrole, imidazole, pyrazole, indole or any C-substituted derivatives of the cyclic secondary amine.

a) contacting the reactants TSA and $nR^1R^2NH$ and $mR^3R^4NH$ and $kR^5R^6NH$ in the presence of a transition metal catalyst forming a reaction mixture;
b) optionally adding a solvent to the reaction mixture;
c) maintaining the reaction mixture at a temperature between about 0° C. to about 250° C.;
d) allowing the reaction to proceed to form $(R^1R^2N)_n(R^3R^4N)_m(R^5R^6N)_k(NSi_3H_{(9-n-m-k)})$;
e) separating the $(R^1R^2N)_n(R^3R^4N)_m(R^5R^6N)_k(NSi_{(9-n-m-k)})$ from the reaction mixture;
wherein the reaction mixture temperature may vary during the synthesis and is maintained such that the temperature of the reaction mixture is not allowed to drop below about 0° C. and not exceed about 250° C.

A method for preparing the compound having the formula:

$(R^1R^2N)_n(R^3R^4N)_k(R^5R^6N)_m(NSi_6H_{(15-n-m-k)})$ where n=1 to 3; m=0 to 3; k=0 to 3; $R^1$, $R^3$, and $R^5$ are independently selected from the group of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^2$, $R^4$, and $R^6$ are independently selected from the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^1R^2N$, $R^3R^4N$ and $R^5R^6N$ can be cyclic secondary amines include aziridine, azetidine, piperidine, pyrrolidine, pyrrole, imidazole, pyrazole, indole or any C-substituted derivatives of the cyclic secondary amine.

a) contacting the reactants TDSA and $nR^1R^2NH$ and $mR^3R^4NH$ and $kR^5R^6NH$ in the presence of a transition metal catalyst forming a reaction mixture;
b) optionally adding a solvent to the reaction mixture;
c) maintaining the reaction mixture at a temperature between about 0° C. to about 250° C.;
d) allowing the reaction to proceed to form $(R^1R^2N)_n(R^3R^4N)_k(R^5R^6N)_m(NSi_6H_{(15-n-m-k)})$;
e) separating the product $(R^1R^2N)_n(R^3R^4N)_k(R^5R^6N)_m(NSi_6H_{(15-n-m-k)})$ from the reaction mixture;
wherein the reaction temperature may vary during the synthesis and is maintained such that the temperature of the reaction mixture is not allowed to drop below about 0° C. and not exceed about 250° C.

A method for preparing the compound having the formula:

where; $R^1$, $R^2$ are independently selected from the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, $R^1R^2N$, can be a cyclic secondary amine selected from the group of aziridine, azetidine, piperidine, pyrrolidine, pyrrole, imidazole, pyrazole, indole or any C-substituted derivatives of the cyclic secondary amine, $R^3$, $R^4$, and $R^5$ are independently selected from H and the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, a cyclic secondary amine selected from the group of aziridine, azetidine, piperidine, pyrrolidine, pyrrole, imidazole, pyrazole, indole or any C-substituted derivatives of the cyclic secondary amine where R is selected from the group of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether.

a) contacting the reactants $NRSiH_2R^3)(SiH_2R^4)(SiH_2R^5)$ and $HNR^1R^2$ in the presence of a transition metal catalyst forming a reaction mixture;
b) optionally adding a solvent to the reaction mixture;
c) maintaining the reaction mixture at a temperature between about 0° C. to about 250° C.;
d) allowing the reaction to proceed to form $N[(SiH_2R^3)(SiH_2R^4)(SiHR^5NR^1R^2)]$;
e) separating the product $N[(SiH_2R^3)(SiH_2R^4)(SiHR^5NR^1R^2)]$ from the reaction mixture;
wherein the reaction mixture temperature may vary during the synthesis and is maintained such that the temperature of the reaction mixture is not allowed to drop below about 0° C. and not exceed about 250° C.

Sample structure for $R^1$ and $R^2$=ethyl; $R^3$, $R^4$ and $R^5$=H.

A method for preparing the compound having the formula:

a) contacting the reactants TSA and $HN(CH_2CH_3)_2$ in the presence of a transition metal catalyst forming a reaction mixture;
b) optionally adding a solvent to the reaction mixture;
c) maintaining the reaction mixture at a temperature between about 0° C. to about 250° C.;
d) allowing the reaction to proceed to form $H_8Si_3N(CH_2CH_3)_2$;
e) separating the $H_8Si_3N(CH_2CH_3)_2$ from the reaction mixture;
wherein the reaction temperature may vary during the synthesis and is maintained such that the temperature of the reaction mixture is not allowed to drop below about 0° C. and not exceed about 250° C.

The terms chlorine free, halogen free, aminochlorine free and aminohalogen free are used herein to define compounds that contain less than 5 ppm of halogen, preferably less than 3 ppm halogen and more preferably less than 1 ppm halogen. The terms halogen and halide include fluorine, chlorine, bromine and iodine. Halogen free products are achieved in the present synthesis because the starting reactants, catalyst and optional solvents of the present invention are halogen free. The terms aminohalide and aminohalogen refer to any amine including but not limited to ammonia, and organic amines which are associated with a halogen. This association may be a salt, a complex or a chemical bond. The terms "reaction vessel" and "reactor" refer to the same equipment, have the same meaning and are used interchangeably herein. The reactor may be a vessel for batch synthesis or a flow through vessel to facilitate a continuous synthesis. The term "reaction mixture" refers to the combination of reactants, catalyst and optionally solvent wherein a reaction takes place to form the product. The terms "halide free" and "halogen free" as used in this disclosure and the claims refers to the level of halogens present from all sources such as but not limited to halogen ions, bound halogens and aminohalogens.

The following method describes the synthesis of aminotrisilylamines comprising:
a) contacting the amine and TSA reactants in the presence of a transition metal catalyst forming a reaction mixture;
b) optionally adding a solvent to the reaction mixture;

c) maintaining the reaction mixture at a temperature between about 0° C. to about 250° C.;
d) allowing the reaction to proceed to form a product;
e) separating the product from the reaction mixture;

The term "maintaining . . . at a temperature" as used herein means heating or cooling as required to produce a temperature within the specified minimum and maximum temperature. The order of addition of amine and silane to the reaction vessel may be either amine first or silane first. When the starting materials are halogen free, the products will be halogen and aminohalogen free.

Heterogeneous catalysts suitable in the present invention include transition metal catalysts and rare earth elements. Catalysts are selected from the group consisting of: Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Yb and U. Preferred catalysts are selected from the group consisting of Ru, Pd, Rh, Ir, Fe, Ni, Pt, Cr, Cu and Au. More preferred catalysts are selected from the group consisting of Rh, Pd, Ru and Pt. A most preferred catalyst is Ru and Ru on carbon. An additional preferred catalyst is Pd on MgO.

Catalysts of the present invention are preferably affixed to a support. The support is a solid with a high surface area. Typical support materials include but are not limited to: alumina, MgO, zeolites, carbon, Monolith cordierite, diatomaceous earth, silica gel, silica/alumina, ZrO and $TiO_2$. Preferred supports are carbon, alumina, silica and MgO. A more preferred support is carbon. Supports have a BET surface area ranging between about 1 $m^2/g$ to about 3,000 $m^2/g$. A preferred range is about 100 $m^2/g$ to about 2,000 $m^2/g$. Metal loading of the catalyst ranges between about 0.01 weight percent to about 50 weight percent. A preferred range is about 0.5 weight percent to about 20 weight percent. A more preferred range is about 0.5 weight percent to about 10 weight percent. Catalysts may be activated by a number of known methods. Heating the catalyst under vacuum is a preferred method. The catalyst may be activated before addition to the reaction vessel or in the reaction vessel prior adding the reactants.

The catalyst may contain a promoter. Promoters are substances which themselves are not catalysts, but when mixed in small quantities with the active catalysts increase their efficiency (activity and/or selectivity). Promoters are usually metals such as Mn, Ce, Mo, Li, Re, Ga, Cu, Ru, Pd, Rh, Ir, Fe, Ni, Pt, Cr, Cu and Au and/or their oxides. They can be added separately to the reactor vessel or they can be part of the catalysts themselves. For example, Ru/Mn/C (ruthenium on carbon promoted by manganese) or Pt/CeO2/Ir/SiO2 (Platinum on silica promoted by ceria and iridium). Some promoters can act as catalyst by themselves but their use in combination with the main catalyst can improve the main catalyst's activity. A catalyst may act as a promoter for other catalysts. In this context, the catalyst can be called a bimetallic (or polymetallic) catalyst. For example, Ru/Rh/C can be called either ruthenium and rhodium on carbon bimetallic catalyst or ruthenium on carbon promoted by rhodium. An active catalyst is a material that acts as a catalyst in a specific chemical reaction.

Catalysts may require activation which is typically carried out under vacuum or under an inert gas or reducing gas such as hydrogen. or helium and at elevated temperatures. Typically catalysts are activated at about 125° C. and at about −14 psig which is about 1 Torr. Dynamic vacuum as used herein describes a vacuum of about 1 Torr. Activation conditions will vary somewhat by the catalyst selected. Conditions for activating the various catalysts are known in the art. Activated catalysts may be stored for future use.

When solvents are used in the present invention, solvents that are non-reactive with the reactants are selected. Solvents are anhydrous and do not deactivate (poison) the catalyst. A non-limiting list of such solvents include: alkanes such as $C_5$ to $C_{20}$ linear, branched or cyclic alkanes and mixtures thereof; alkenes such as 1-octadecene, cyclooctadiene and cyclohexene; chloroalkanes such as methylene chloride and ethylene chloride; arenes such as toluene, xylene, mesitylene and naftalene and heterocycles such as quinoline and pyridine and mixtures thereof. A preferred solvent is n-octadecane. Preferably, the solvent should be selected such that its boiling point differs from the boiling point of the product compound by about 10° C.

Inert gas used in the present invention is not reactive under the reaction conditions. A non-limiting list of inert gases includes: helium, argon and nitrogen. A preferred gas is helium.

A Parr autoclave equipped with a mechanical stirred is a suitable reaction vessel. For synthesis of the monosubstituted trisilylamine and monosubstituted tridisilylamine, the molar ratio of TSA or TDSA to amine at the start of the reaction is within the range of about 0.5 to about 5 preferably about 1 to about 3. For polysubstituted TSA and polysubstituted TDSA, the molar ratio of TSA or TDSA to amine at the start of the reaction is within the range of about 0.1 to about 0.9.

The term cryotrapping means condensing a gaseous material in a cryotrap.

Example 1

Diethylaminosilyl-bis-Disilylamine synthesis in a pressurized reactor by the reaction between trisilylamine (TSA) and diethylamine catalyzed by commercially available Ruthenium on carbon catalyst: A 0.3 L autoclave equipped with a mechanical stirrer, a thermocouple, a pressure gauge and a pressure transducer and 3 metering valves was charged with 5.3 g (0.0025 mmol of ruthenium) of 5% weight ruthenium on carbon catalyst. The reactor was then heated under dynamic vacuum at about 125° C. for 3 hr. Dynamic vacuum as used herein describes a vacuum of about 1 Torr. After cooling to room temperature, 14.8 g (0.202 mol) of diethylamine was added to the reactor and then it was cooled to about −130° C. in a liquid nitrogen bath. 40 g (0.372 mol) of trisilylamine was transferred to the reactor. The reactor was then gradually heated to about 100° C. After stirring at about 400 rpm for 65 rpm, pressure increased about 300 psi. The pressure increase is proportional to the amount of hydrogen (and product) formed, so it will vary depending on the scale of the reaction. The reaction is complete when the pressure stops increasing. It may be desirable to stop the reaction before it is complete. The reactor was cooled to room temperature ("RT"). Volatiles were collected in a cryotrap at liquid nitrogen temperature in a SSLB. The reactor pressure went down to 50 Torr.

The 1-Diethylaminosilyl-bis-Disilylamine was recovered from the reaction vessel.

The resulting solution contained 30% (11.3 g) of Diethylaminosilyl-bis-Disilylamine. The non-isolated yield was 30%.

Structure: Diethylaminosilyl-Bis-Disilylamine:

General Synthesis TSA Amine Compounds:
a) amine substituted TSA compounds are synthesized in a pressurized reactor by the reaction between trisilylamine (TSA) and an amine catalyzed by a transition metal catalyst: An autoclave or similar pressurized reactor vessel equipped with a mechanical stirrer, a thermocouple, a pressure gauge and a pressure transducer and 3 metering valves is charged with a transition metal catalyst. The reactor is then heated under dynamic vacuum at about 125° C. for 3 hr to activate the catalyst. The catalyst may be activated before addition to the reaction vessel or in the reaction vessel prior adding the reactants. If the catalyst is activated before addition to the reaction vessel then the prior heating step under dynamic vacuum at about 125° C. for 3 hr to activate the catalyst is omitted. After cooling to room temperature, the amine is added to the reactor and then it is cooled to −130° C. in a liquid nitrogen bath. The appropriate amount of trisilylamine is transferred to the reactor. The reactor temperature is maintained to not drop below 0° C. and not allowed to exceed 250° C. With stirring from about 5 min to about 2 days, the reactor pressure increases until the reaction is complete. The pressure increase is proportional to the amount of hydrogen (and product) formed. Therefore, reactor pressure will vary depending on the scale, amount of each reactant, of the reaction and the size of the reactor. The reaction is complete when the pressure stops increasing. After the reaction is complete, the reactor is cooled to RT. Volatiles are collected in a cryotrap at liquid nitrogen temperature in a SSLB and the reactor pressure decreases to between about 40 Torr to about 100 Torr. To produce monosubstituted TSA/amine compounds, the molar ratio of TSA/amine is from about 0.5 to about 5 and more preferably from about 1 to about 3. To produce polysubstituted TSA/amine compounds, the molar ratio of TSA/amine is from about 0.1 to about 0.9. The lower the ratio, the greater the degree of substitution of amine on the TSA compound will occur.

A preferred catalyst for the synthesis of TSA/amine compounds is selected from the group consisting of Ru, Pd, Rh, Ir, Fe, Ni, Pt, Cr, Cu and Au. A most preferred catalyst is ruthenium.

General Synthesis TDSA Amine Compounds:
a) amine substituted TDSA compounds are synthesized in a pressurized reactor by the reaction between tridisilylamine (TDSA) and an amine catalyzed by a transition metal catalyst:
An autoclave or similar pressurized reactor vessel equipped with a mechanical stirrer, a thermocouple, a pressure gauge and a pressure transducer and 3 metering valves is charged with a transition metal catalyst. The reactor is then heated under dynamic vacuum at about 125° C. for 3 hr to activate the catalyst. The catalyst may be activated before addition to the reaction vessel or in the reaction vessel prior adding the reactants. If the catalyst is activated before addition to the reaction vessel then the prior heating step under dynamic vacuum at about 125° C. for 3 hr to activate the catalyst is omitted. After cooling to room temperature, the amine is added to the reactor and then it is cooled to −130° C. in a liquid nitrogen bath. The appropriate amount of trisilylamine is transferred to the reactor. The reactor temperature is maintained to not drop below about 0° C. and not allowed to exceed about 250° C. With stirring from about 5 min to about 2 days, the reactor pressure increases until the reaction is complete. The pressure increase is proportional to the amount of hydrogen (and product) formed. Therefore, reactor pressure will vary depending on the scale, amount of each reactant, of the reaction and the size of the reactor. The reaction is complete when the pressure stops increasing. After the reaction is complete, the reactor is cooled to RT. Volatiles are collected in a cryotrap at liquid nitrogen temperature in a SSLB and the reactor pressure decreases to between about 40 Torr to about 100 Torr. To produce monosubstituted TDSA/amine compounds, the molar ratio of TSA/amine is from about 0.5 to about 5 and more preferably from about 1 to about 3. To produce polysubstituted TDSA/amine compounds, the molar ratio of TSA/amine is from about 0.1 to about 0.9. The lower the ratio, the greater the degree of substitution of amine on the TDSA compound will occur.

A preferred catalyst for the synthesis of TDSA/amine compounds is selected from the group consisting of Ru, Pd, Rh, Ir, Fe, Ni, Pt, Cr, Cu and Au. A most preferred catalyst is ruthenium.

The term "non-isolated yield" means the yield is determined by weighing the reaction crude and estimating the amount of product by its chromatogram. The term "isolated yield" means the product was purified and weighed with the percent yield being determined by the percent of theoretical the amount weighed represents.

The amino trisilylamines and amino tridisilylamines of the present invention are used as precursors for vapor deposition methods. Disclosed herein are methods of using the disclosed precursors for vapor deposition methods. The disclosed methods provide for the use of the precursors for deposition of silicon-containing films. The disclosed methods may be useful in the manufacture of semiconductor, photovoltaic, LCD-TFT, or flat panel type devices. The method includes: introducing the vapor of the disclosed precursors into a reactor having at least one substrate disposed therein: and using a vapor deposition process to deposit at least part of the disclosed precursor onto the substrate to form a Si-containing layer.

The disclosed methods also provide for forming a bimetal containing layer on a substrate using a vapor deposition process and, more particularly, for deposition of $SiMN_x$ and $SiMO_x$ films wherein x is 0-4, and $SiMO_xN_y$ films, wherein x+y is 0 to 4 and M is a metal from the group Ta, Hf, Zr, Ti, Ni, Mn, Ge, B, Nb, Mg, Al, Sr, Y, Ba, Ca, As, Sb, Bi, Sn, Pb, Co, lanthanides (such as Er), or combinations thereof. The general $SiMO_x$, $SiMO_x$ or $SiMO_xN_y$ terminology covers various relative concentrations of Si and M in the range of Si/(Si+M) is about 5% to about 95%.

The disclosed methods of forming silicon-containing layers on substrates may be useful in the manufacture of semiconductor, photovoltaic, LCD-TFT, or flat panel type devices. The disclosed precursors may deposit Si-containing films using any vapor deposition methods known in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process, remote plasma CVD (RP-CVD) UV assisted CVD, flowable CVD (FCVD)), radicals incorporated CVD, and combinations thereof. Exemplary ALD methods include thermal ALD, plasma enhanced ALD (PEALD), spatial isolation ALD, hot-wire ALD (HWALD), radicals incorporated ALD, UV assisted ALD and combinations thereof. Super critical fluid deposition may also be used. The disclosed methods may also be used in the flowable PECVD deposition processes described in U.S. Pat. App. Pub. No. 2014/0051264 to Applied Materials, Inc., the contents of which is incorporated herein in its entirety. The deposition method is preferably ALD, spatial ALD, PE-ALD or flowable CVD (F-CVD).

The vapor of the precursor is introduced into a reaction chamber containing at least one substrate. The temperature and the pressure within the reaction chamber and the temperature of the substrate are held at conditions suitable for vapor deposition of at least part of the precursor onto the substrate. In other words, after introduction of the vaporized precursor into the chamber, conditions within the chamber are such that at least part of the vaporized precursor is deposited onto the substrate to form the silicon-containing film. A co-reactant may also be used to help in formation of the Si-containing layer. The co-reactant may be introduced simultaneously or separately sequentially from the precursors and is selected from $O_2$, $O_3$, O radicals and ions, NO, $N_2O$, $H_2O$, $H_2O_2$, $CO_2$, CO, carboxylic acid, formalin, alcohols, diols, $NH_3$, hydrazines (substituted or not, such as UDMH, terbutylhydrazine), amines (such as DMA, TMA, DEA, TEA, TB, $NH_2$), diamines, N radicals and ions, $H_2$ and mixtures thereof.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems such as spatial ALD chambers, roll to roll ALD chambers. All of these exemplary reaction chambers are capable of serving as an ALD reaction chamber. The reaction chamber may be maintained at a pressure ranging from about 1 mTorr to about 760 Torr. In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder, controlling the temperature of the reactor wall, or controlling the temperature of the substrate itself. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 200° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The type of substrate upon which the silicon-containing film will be deposited will vary depending on the final use intended. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, Ge, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, porous carbon doped silicon oxide layers, silicon carbo-nitride, hydrogenerated silicon carbide, or combinations thereof. Additionally, the wafers may include copper layers, tungsten layers or metal layers (for example platinum, palladium, nickel, rhodium, gold, Cobalt, germanium, antimony, tellurium, tin, ruthenium and their alloys). The wafers may include barrier layers, such as manganese, manganese oxide, nitrides of Ta, W, Ti, V, Zr, Hg, Nb, Mo, Mn and Ru. Nitride may be C-doped nitride. Plastic layers, such as poly(3,4-ethylenedioxythiophene)poly(styrenesulfonate) [PEDOT:PSS] may also be used. The film may be deposited over an organic film, such as a photoresist layer, an amorphous carbon layer, or a polyimide film. The layers may be planar or patterned. In some embodiments, the substrate may include layers of oxides which are used as dielectric materials in MIM, DRAM, RERAM, phase change RAM, or FeRam technologies (for example, Zr, Hg, Ti, Nb, Mo, Al, Ta, lanthanides, rare earths and mixed ternary or binaryoxides thereof) or from nitride-based films (for example, TaN) that are used as an adhesion barrier between copper and the low-k layer. The disclosed processes may deposit the silicon-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may have 3D patterns or microstructures such as holes and trenches or a line. The deposition may be selective to specific areas on the substrate, or selective to certain exposed materials. For example, the growth may be inhibited on certain parts of the substrate covered with self aligned monolayers ("SAM"). Throughout the specification and claims, the wafer and any associated layers thereon are referred to as substrates.

The disclosed precursors may be supplied either in neat form or in a blend with a suitable solvent, such as toluene, ethyl benzene, xylene, mesitylene, decane, dodecane, octane, hexane, pentane, tertiary amines, tetrahydrofuran, ethylmethylketone, decalin, or others. The disclosed precursors may be present in varying concentrations in the solvent. For example, the resulting concentration may range from approximately 0.05 M to approximately 2 M.

The neat or blended precursors are introduced into a reactor in vapor form by conventional means, such as tubing and/or flow meters. The precursor in vapor form may be produced by vaporizing the neat or blended precursor solution through a conventional vaporization step such as, bubbling, vapor draw or by using a sublimator such as the one disclosed in PCT Publication WO2009/087609 to Xu et al. The neat or blended precursor may be fed in liquid state to a vaporizer where it is vaporized before it is introduced into the reactor (direct liquid injection). When present, the carrier gas may include, but is not limited to, Ar, He, $N_2$, or $H_2$ and mixtures thereof. The carrier gas and precursor are then introduced into the reactor as a vapor.

If necessary, the container may be heated to a temperature that permits the precursor to be in its liquid or solid phase and to have a sufficient vapor pressure. The container may be maintained at temperatures in the range of, for example, 0-150° C. Those skilled in the art recognize that the temperature of the container may be adjusted in a known manner to control the vapor pressure of the precursor vaporized and the concentration in the process chamber.

The film obtained by a vapor deposition method can be further treated by various methods such as annealing, reactive annealing, UV curing, e-beam curing and radical annealing. The film composition and structure can be significantly affected by this step.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

Although the description above contains much specificity, these should not be construed as limiting the scope of the invention but as merely providing illustrations of some of the presently preferred embodiments of this invention. Various other embodiments and ramifications are possible within its scope. It will be understood that many additional changes in the details, materials, steps, and arrangement of parts, which have been herein described and illustrated in order to explain the nature of the invention, may be made by those skilled in the art within the principle and scope of the invention as expressed in the appended claims.

We claim:

1. A compound having the formula:

where n=1 to 3; m=0 to 3; k=0 to 3; $R^1$, $R^3$, and $R^5$ are independently selected from H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$, $R^4$, and $R^6$ are independently selected from a linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^1R^2N$, $R^3R^4N$ and $R^5R^6N$ $R^1R^2N$, $R^3R^4N$ and $R^5R^6N$ can be cyclic secondary amines independently selected from aziridine, azetidine, piperidine, pyrrolidine, pyrrole, imidazole, pyrazole, indole or any C-substituted derivatives of the cyclic secondary amine; and excluding compounds having the formula $C_{18}H_{48}N_4Si_3$; $C_{15}H_{41}N_3Si_3$; $C_6H_{21}NSi_3$ and $C_7H_{23}NSi_3$ or the said compounds exclude the following known compound: $[(SiH_3)_2N]_2SiH_2$.

2. A compound having the formula:

where n=1 to 3; m=0 to 3; k=0 to 3; $R^1$, $R^3$, and $R^5$ are independently selected from H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$, $R^4$, and $R^6$ are independently selected from a linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^1R^2N$, $R^3R^4N$ and $R^5R^6N$ $R^1R^2N$, $R^3R^4N$ and $R^5R^6N$ can be cyclic secondary amines independently selected from aziridine, azetidine, piperidine, pyrrolidine, pyrrole, imidazole, pyrazole, indole or any C-substituted derivatives of the cyclic secondary amine.

3. A compound having the formula:

where $R^1$, $R^2$ are independently selected from H, a linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, trimethyl silyl, or linear or branched $C_1$ to $C_6$ alkyl-substituted silyl; $R^3$, $R^4$, and $R^5$ are independently selected from H, a linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; and $R^1R^2N$ can be a cyclic secondary amine selected from aziridine, azetidine, piperidine, pyrrolidine, pyrrole, imidazole, pyrazole, indole or any C-substituted derivatives of the cyclic secondary amine.

4. The compound of claim 3 having the formula:

5. The compound of claim 3 wherein $R^1$, $R^2$ are independently selected from the group consisting of H, methyl, ethyl, iso-propyl, and t-butyl; or $NR^1R^2$ are a cyclic saturated or unsaturated cyclic amine with 3 to 8 carbon atoms, when $R^1$ is H then $R^2$ cannot be methyl or ethyl.

6. The compound of claim 3 wherein $R^1$, $R^2$ are ethyl.

7. The compound of claim 3 wherein $R^1$, $R^2$ are iso-propyl.

* * * * *